United States Patent
Abramsohn et al.

[11] Patent Number: 6,166,550
[45] Date of Patent: Dec. 26, 2000

[54] CHARGE MEASURING INSTRUMENT

[75] Inventors: Dennis A. Abramsohn, Pittsford; Lois A. Eckstrom, Williamson; Diane M. Foley, Palmyra, all of N.Y.

[73] Assignee: Xerox Corporation, Stamford, Conn.

[21] Appl. No.: 09/192,900

[22] Filed: Nov. 16, 1998

[51] Int. Cl.[7] .................................................. G01N 27/61
[52] U.S. Cl. ............................................ 324/452; 324/459
[58] Field of Search ..................................... 324/459, 455, 324/452, 72; 399/48, 50, 73, 168–176

[56] References Cited

U.S. PATENT DOCUMENTS

| | | | |
|---|---|---|---|
| 3,619,615 | 11/1971 | Fish | 250/106 |
| 3,788,739 | 1/1974 | Coriale | 355/17 |
| 4,087,171 | 5/1978 | Yano | 355/14 |
| 4,215,930 | 8/1980 | Miyakawa et al. | 355/14 D |
| 4,302,721 | 11/1981 | Urbanek et al. | 324/226 |
| 4,355,885 | 10/1982 | Nagashima | 355/14 CH |
| 4,626,096 | 12/1986 | Ohtsuka et al. | 355/14 D |
| 4,734,649 | 3/1988 | Barnaby | 324/376 |
| 4,814,703 | 3/1989 | Carr et al. | 324/207 |
| 4,862,065 | 8/1989 | Pazda et al. | 324/65 R |
| 4,885,543 | 12/1989 | Smith | 324/452 |
| 5,066,918 | 11/1991 | Pazda et al. | 324/452 |
| 5,235,394 | 8/1993 | Mills et al. | 355/284 |
| 5,285,241 | 2/1994 | Scheuer | 355/208 |
| 5,287,061 | 2/1994 | Dechene et al. | 324/454 |
| 5,436,705 | 7/1995 | Raj | 355/246 |
| 5,508,622 | 4/1996 | Gatzlaff et al. | 324/558 |
| 5,552,704 | 9/1996 | Mallory et al. | 324/233 |
| 5,565,963 | 10/1996 | Tsujita et al. | 355/208 |
| 5,585,730 | 12/1996 | Pazda et al. | 324/452 |
| 5,666,618 | 9/1997 | Lee et al. | 399/254 |
| 5,679,883 | 10/1997 | Wedeven | 73/10 |
| 5,717,978 | 2/1998 | Mestha | 399/46 |
| 5,749,019 | 5/1998 | Mestha | 399/46 |
| 5,754,918 | 5/1998 | Mestha et al. | 399/48 |
| 5,773,989 | 6/1998 | Edelman et al. | 324/765 |
| 5,795,990 | 8/1998 | Gitis et al. | 73/9 |
| 5,805,961 | 9/1998 | Mizoe et al. | 399/174 |
| 5,822,662 | 10/1998 | Raj et al. | 399/260 |
| 5,842,082 | 11/1998 | Hyakutake et al. | 399/66 |

Primary Examiner—Glenn W. Brown
Assistant Examiner—Vincent Q. Nguyen
Attorney, Agent, or Firm—Andrew D. Ryan

[57] ABSTRACT

An apparatus for obtaining measurements of the charge on a surface of a member during a period of time while applying a charge to the surface of the member is provided. The apparatus includes a frame. The member is rotatably secured to the frame. The apparatus also includes a charging device for applying the charge to the member. The charging device includes a charging device portion thereof positioned proximate to an external periphery of the member. The apparatus also includes a mechanism for rotating the member. The mechanism is operably associated with the frame. The apparatus also includes a charge measuring device operably associated with the support for measuring an electrical field emanating from the member. The charge measuring device includes a measuring device portion thereof positioned proximate to a measured position on an external periphery of the member. The mechanism is cooperable with the member to rotate the member. The charge measuring device is adapted to measure a charge at the measured position after the member is so rotated.

20 Claims, 6 Drawing Sheets

| SAMPLE ON DRUM | AGAINST SELF | AGAINST TEFLON BLADE | SURFACE RESISTIVITY LOG OHMS |
|---|---|---|---|
| CONTROL COATED OFFSET | -40V | +150 V | 10.3 |
| CONDUCTIVIZED COATED OFFSET | <-10V | <+10V | 9.0 |
| UNCOATED ACID PAPER | <-10V | +60V | 10.2 |
| UNCOATED ALKALINE PAPER | -50V | +200V | 10.4 |
| CONDUCTIVIZED UNCOATED ALKALINE PAPER | <-10V | +100V | 10.0 |

FIG. 3

CHARGE MEASURING INSTRUMENT

This invention relates generally to an apparatus and a method for measuring charge, and more particularly concerns measuring the triboelectric charge on a substrate.

Cross reference is made to the following application filed concurrently herewith: U.S. Application Ser. No. (09/192,760), entitled "Charge Measuring Instrument for Flexible Materials", by Dennis A. Abramsohn et al., the relevant portions thereof incorporated herein by reference.

The features of the present invention are useful in any machine which has concerns regarding the triboelectric charges within the machine. One such machine is a printing machine, for example electrophotographic printing machine.

In the process of electrophotographic printing, a photoconductive surface is charged to a substantially uniform potential. The photoconductive surface is image wise exposed to record an electrostatic latent image corresponding to the informational areas of an original document being reproduced. This records an electrostatic latent image on the photoconductive surface corresponding to the informational areas contained within the original document. Thereafter, a marking material such as toner particles is transported into contact with the electrostatic latent image in a region known as the development zone. Toner particles are attracted from the magnetic roller to the latent image. The resultant toner powder image is then transferred from the photoconductive surface to a copy sheet and permanently affixed thereto. The foregoing generally describes a typical mono-color single component development electrophotographic copying machine.

Printing machines are widely used to print written material and documents of all types. The printing machines may be of many types including, but not limited to, gravature or offset type ink printing, thermal inkjet printing, bubble jet printing, direct electrostatic printing and electrostatographic or xerographic printing. Xerographic printing can be done with wet or dry marking materials.

The printing machines may utilize any type of substrate on which to print. Typically, printing machines use paper on which to print. The paper comes typically in two forms, that of a continuous roll and in single sheets. The sheets or rolls are typically fed by rollers and baffles through various parts of the printing or xerographic process. Static electricity causes many substrate handling problems and is particularly a problem with various papers. The static electricity is particularly a problem on sheet-type printing machines. The static electricity causes the sheets to adhere to each other and rather than feed seriatim or one at a time, the sheets feed in an overlapped basis because of the static electricity which causes adjacent sheets to be secured to each other. Such adherence of adjoining sheet leads to jams within the printing machine and resultant down time for the printing machine. Further, in operations in which collation or sorting of sheets occurs, the static electricity may cause for the undesired reordering of sheets which may make a printed copy inaccurate or include multiple or missing sheets.

Static electricity becomes even more of a problem in an electrostatographic or xerographic printing machine, or any machine in which static electricity is utilized for part of the printing process. Further, in xerographic and other types of electrostatographic printing, corona generating devices are included within the machine which may create additional static electricity within the machine.

Further, the mere existence of components which rub or contact the paper as it passes through the paper path within the printing machine may generate static electricity. The baffles, chutes and rollers within a printing machine may be made of any of a number of metal or plastic or synthetic rubber materials which may generate exceedingly large amounts of static electricity when in contact with, and rubbing against, paper. Coatings and additives to the copy sheets may further increase or decrease the static electricity generated through the rubbing process within the printing machine. Further adjacent sheets of paper, when in contact during the printing process, either while stacking or unstacking a set of sheets, may likewise generate static electricity.

These problems are exacerbated by the use of high speed printers. Xerographic and statiographic printers are now available at speeds of 200 copies per minute or greater. Offset gravature-type printing speeds can be many times greater than those. As the translational speed of paper through the printing machine becomes faster and faster, the levels of static electricity that can be generated likewise increase.

In attempt to alleviate these problems with static electricity in the printing process, paper has been selected to minimize static electricity. Further additives are added to the paper and coatings to the paper to minimize the static electricity build-up within the printing process. Paper can now be chosen by surface resistivity and charge acceptance. These characteristics of paper may assist the operator of the printing machine in the proper utilization of paper.

The attempts to categorize papers and to provide additives and coatings to paper to minimize the effect of static electricity has several problems. The current measuring systems of measuring surface resistivity and charge acceptance of a sheet of paper cannot accurately predict the severity or location of static buildup within the printing process. Different paper characteristics have different triboelectric behavior that is not predicted by surface resistivity measurements. A need therefore exists to reproducibly generate and measure static electricity and its effect on paper. If accurate measurements were able to be made of paper as it contacts various materials, machine designs could be improved by taking into account the interrelationship of various materials during the printing process.

Electrical properties of other materials and components in addition to flexible material such as sheets require exacting tolerances which are difficult to measure. For certain type of components used in the printing art, namely photoconductive drums, donor rolls such as those used in hybrid scavengeless development as disclosed in U.S. Pat. No. 4,868,600 to Hayes et al., the relevant portions thereof incorporated herein by reference and in rolls for direct electrostatic printing such as those disclosed in U.S. Pat. No. 4,755,837 to Schmidlin et al., the relevant portions thereof incorporated herein by reference the electrical properties of these components are critical.

Electrostatic printing rolls, donor rolls, and photoconductive drums require particularly specific electrical properties. In particular, electrostatic rolls and donor rolls may require a permittivity of a very narrow range for proper operation of the roll. Furthermore, donor rolls and electrostatic print rolls, due to the manufacturing processes involved in making the rolls, may have electrical properties including permittivity that vary widely within a particular roll compounding the difficulty in obtaining accurate electrical property measurements.

The following disclosures may be relevant to various aspects of the present invention:

U.S. Pat. No. 5,805,961
Patentee: Mizoe et al.
Issue Date: Sep. 8, 1998

U.S. Pat. No. 5,795,990
Patentee: Gitis et al.
Issue Date: Aug. 18, 1998

U.S. Pat. No. 5,679,883
Patentee: Wedeven
Issue Date: Oct. 21, 1997

U.S. Pat. No. 5,552,704
Patentee: Mallory et al.
Issue Date: Sep. 3, 1996

U.S. Pat. No. 5,508,622
Patentee: Gatzlaff et al.
Issue Date: Apr. 16, 1996

U.S. Pat. No. 4,862,065
Patentee: Pazda et al.
Issue Date: Aug. 29, 1989

U.S. Pat. No. 4,814,703
Patentee: Carr et al.
Issue Date: Mar. 21, 1989

U.S. Pat. No. 4,734,649
Patentee: Barnaby
Issue Date: Mar. 29, 1988

U.S. Pat. No. 4,302,721
Patentee: Urbanek et al.
Issue Date: Nov. 24, 1981

The relevant portions of the foregoing disclosures may be briefly summarized as follows:

U.S. Pat. No. 5,805,961 discloses a charging member, which electrically charges an object to be charged by being placed in contact with the object to be charged and by being applied with a voltage. The charging member includes an electroconductive base and brush bristles to come into contact with the object to be charged and the brush bristles include at least one of etching fibers and divided fibers.

U.S. Pat. No. 5,795,990 discloses a tester having a horizontal base with a vertical column that supports vertical guides for guiding a carriage that supports a rotary drive mechanism for an upper specimen which is secured in a chuck and engages a lower specimen supported by an interchangeable bowl. The tester is also provided with a computerized measuring system for precisely measuring characteristics to be tested. The main distinguishing feature of the tester of the invention is a that a flexible coupling that may have at least one degree of freedom (preferably three) is installed in a link between a rotary motion unit and the chuck for fixing the upper specimen. In other words, the upper specimen is fixed in a self-aligning manner so that its flat working surface is always maintained in full surface-to-surface contact with the lower specimen. In addition, a provision of the flexible coupling in the link between the drive unit and the zone of friction contact makes it possible to decrease strictness in requirement of manufacturing accuracy of guides and other parts of the tester.

U.S. Pat. No. 5,679,883 discloses a process and apparatus that allows a comprehensive evaluation of tribological materials. Such materials include lubricants (liquid, solid and gaseous materials) and load bearing surfaces (bulk materials, surface treatments and coatings). The process and apparatus enable a meaningful characterization of these materials in a way that connects basic lubrication, wear and failure mechanisms with machine hardware in its operational setting.

U.S. Pat. No. 5,552,704 discloses a method and apparatus for performing conductance measurements on a sample using an eddy current probe, without the need for measurement or knowledge of the separation between probe and sample. The probe comprises sense and drive coils mounted in close proximity to each other (or a single coil which functions as both a sense and drive coil), circuitry for producing AC voltage in the drive coil, and a meter for measuring in-phase and quadrature components of induced voltage in the sense coil. Look-up table data can be generated for use in subsequent measurements on samples of unknown conductance by performing eddy current measurements on samples having different known conductances to generate reference lift-off curves, processing the reference lift-off curves to determine a conductance function relating each known conductance to a location along a selected curve, and storing conductance values determined by the conductance function for different points on the selected curve as the look-up table data. An unknown sample conductance can then be determined by generating a lift-off curve from voltage measurements at different probe separations from the sample, determining a new intersection voltage pair representing the intersection of the lift-off curve with the selected curve, and determining the unknown conductance as a look-up table value indexed by the new intersection voltage pair.

U.S. Pat. No. 5,508,622 discloses a detector for continuously monitoring the integrity of a coating on a piece of material. The detector includes an upper bar and a lower bar held near the surfaces of the material. Each bar carries multiple conductive probes in contact with the corresponding surface and electrically connected to an electronic detection circuit. Adjacent probes are connected to electric terminals having different voltage potentials. When probes from the same bar carrying different voltages short together, such as by contacting the surface of conductive sheet material, the detection circuit signals an insufficiently coated area has been found. The short between probes must be large enough to cause a short for more than a predetermined time. The upper probe bar is rotatable to prevent damage.

U.S. Pat. No. 4,862,065 discloses a web roller with at least two electrodes that are positioned parallel to each other on the roller surface end parallel to the longitudinal axis of the roller. Slip rings provide individual electrical connections to the electrodes. The electrodes are spaced apart a distance which permits both electrodes to be in contact with a web of sheet material of the type having a conductive center sandwiched between layers of insulating sheet. A position detector, positioned to detect the rotation of the roller, provides a pulse signal of a known magnitude to one of the electrodes, through a slip ring, when the electrodes are in contact with the web of sheet material. A sensor coupled to the other electrode, through a slip ring, receives the pulse signal after it has passed through the sheet material located between the two electrodes. The magnitude of the received pulse is a function of the resistivity of the sheet material.

U.S. Pat. No. 4,814,703 discloses a sensor including an eddy current loop and an ultrasonic transducer transmitting along a common axis is placed against a second surface of a graphite/epoxy composite structure whose first surface has been formed over the surface of a steel model. The eddy current coil can produce a signal measuring the separation between the sensor and the surface of the steel model, and the ultrasonic transducer can produce a signal representing the thickness of the graphite/epoxy composite panel. The distance and thickness signals are passed to electrical circuitry that computes their difference and displays the calibrated result as a measure of the gap between the steel model and the graphite/epoxy tool.

U.S. Pat. No. 4,734,649 discloses a core holder for making petro-physical measurements of core samples from a borehole. The core holder is designed to make resistivity measurements and fluid-flow tests under reproduced conditions of in-situ fluid saturation, reservoir pressure and reservoir temperature.

U.S. Pat. No. 4,302,721 discloses an instrument for computing resistivity based upon measurements of thickness and conductance. A conductance transducer is a solenoid in an annular ferrite cup connected to a tank circuit for an eddy current measurement of conductance. Within the center of the annular ferrite cup concentric acoustic wave sending and receiving channels are disposed for making an acoustic pressure wave measurement which is used for a thickness measurement using two gauge heads, spaced on opposite sides of an article to be measured. Each gauge head contains identical conductance and thickness transducers. The thickness measurement is divided by the conductance measurement to derive resistivity All of the above references are hereby incorporated by reference.

SUMMARY OF THE INVENTION

In accordance with one aspect of the present invention, there is provided an apparatus for obtaining measurements of the charge on a surface of a member during a period of time while applying a charge to the surface of the member. The apparatus includes a frame. The member is rotatably secured to the frame. The apparatus also includes a charging device for applying the charge to the member. The charging device includes a charging device portion thereof positioned proximate to an external periphery of the member. The apparatus also includes a mechanism for rotating the member. The mechanism is operably associated with the frame. The apparatus also includes a charge measuring device operably associated with the support for measuring an electrical field emanating from the member. The charge measuring device includes a measuring device portion thereof positioned proximate to a measured position on an external periphery of the member. The mechanism is cooperable with the member to rotate the member. The charge measuring device is adapted to measure a charge at the measured position after the member is so rotated.

In accordance with another aspect of the present invention, there is provided an apparatus for measuring the permittivity of a member by obtaining measurements of the charge on a surface of the member after a period of time after applying a charge to the surface of the member. The apparatus includes a frame. The member is rotatably secured to the frame. The apparatus also includes a charging device for applying the charge to the member. The charging device includes a charging device portion thereof positioned proximate to an external periphery of the member. The apparatus also includes a mechanism for rotating the member. The mechanism is operably associated with the frame. The apparatus also includes a charge measuring device operably associated with the support for measuring an electrical field emanating from the member. The charge measuring device includes a measuring device portion thereof positioned proximate to a measured position on an external periphery of the member. The apparatus also includes a position measuring device operably associated with the material for accurately measuring the rotation of the material and a controller. The controller controls at least one of the at least one of the charging device, the mechanism and the charge measuring device. The mechanism is cooperable with the member to rotate the member to a position proximate the measuring device portion of the charge measuring device. The measurement of the permittivity of the member is obtained by obtaining a first voltage measurement of the measured position, rotating the member for an elapsed time defining at least one complete revolution of the member, obtaining a second voltage measurement of the measured position, and utilizing the first voltage measurement, the second voltage measurement, and the elapsed time to calculate permittivity of the member.

Pursuant to yet another aspect of the present invention, there is provided a method for measuring the permittivity of a member. The method includes the steps of applying a charge to a first position on a periphery of the member, rotating the member, measuring a first charge on the first position on the periphery of the member after rotating the member, rotating the member a number of revolutions, measuring a time required for rotating the member the number of revolutions, measuring a second charge on the first position on the periphery of the member after rotating the member the number of revolutions, and calculating the permittivity of the member based on the time required, the first charge, and the second charge.

IN THE DRAWINGS

Other features of the present invention will become apparent as the following description proceeds and upon reference to the drawings, in which:

FIG. 3 is a table of recorded voltages measured utilizing the charge measurement device of FIG. 1 on various substrates in contact with other materials;

DETAILED DESCRIPTION

While the present invention will be described in connection with a preferred embodiment thereof, it will be understood that it is not intended to limit the invention to that embodiment. On the contrary, it is intended to cover all alternatives, modifications, and equivalents as may be included within the spirit and scope of the invention as defined by the appended claims.

Figure 5:
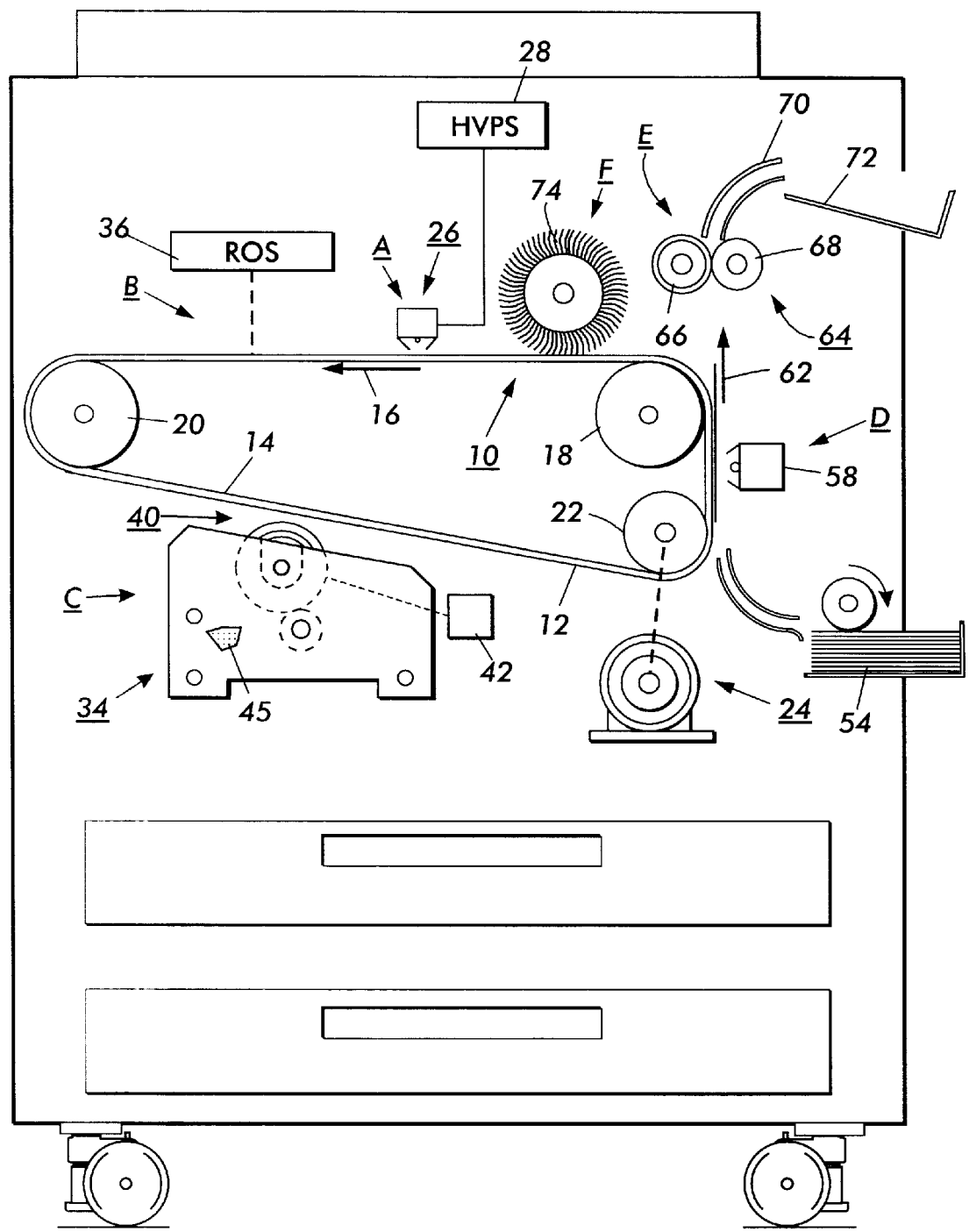
FIG. 5 is a schematic elevational view of an electrophotographic printing machine which may benefit from the charge measuring device of the present invention.

For a general understanding of the illustrative electrophotographic printing machine which may benefit from the charge measuring device of the present invention therein, reference is made to the drawings. In the drawings, like reference numerals have been used throughout to designate identical elements. FIG. 5 schematically depicts the various components of an electrophotographic printing machine. Although charge measuring device of the present invention may assist in the selection of substrates and components for use in the illustrative printing machine, it will become evident that the charge measuring device is equally well suited for use with a wide variety of machines and are not necessarily limited in its application to the particular embodiment shown herein.

Referring now to FIG. 5, the electrophotographic printing machine shown employs a photoconductive belt 10, although photoreceptors in the form of a drum are also known, and may be substituted therefor. The belt 10 has a photoconductive surface 12 deposited on a conductive substrate 14. Belt 10 moves in the direction of arrow 16 to advance successive portions thereof sequentially through the various processing stations disposed about the path of movement thereof. Motor 24 rotates roll 22 to advance belt 10 around rolls 18, 20 and 22 in the direction of arrow 16. Belt 10 is coupled to motor 24 by suitable means such as a drive.

Initially successive portions of belt 10 pass through charging station A. At charging station A, a corona generating device, indicated generally by the reference numeral 26, charges the belt 10 to a selectively high uniform electrical potential, preferably negative. Any suitable control, well known in the art including for example HVPS 28, may be employed for controlling the corona generating device 26.

In a digital printing machine as shown in FIG. 5, the belt 10 passes through imaging station B where a ROS (Raster Optical Scanner) 36 may lay out the image in a series of horizontal scan lines with each line having a specific number of pixels per inch. The ROS 36 may include a laser (not shown) having a rotating polygon mirror block associated therewith. The ROS 36 exposes the photoconductive surface 12 of the belt.

It should be appreciated that the printing machine may alternatively be a light lens copier. In a light lens copier a document to be reproduced is placed on a platen, located at the imaging station, where it is illuminated in known manner by a light source such as a tungsten halogen lamp. The document thus exposed is imaged onto the drum by a system of mirrors. The optical image selectively discharges the surface of the drum in an image configuration whereby an electrostatic latent image of the original document is recorded on the drum at the imaging station.

At development station C, a development system or unit, indicated generally by the reference numeral 34 advances developer materials into contact with the electrostatic latent images. Preferably, the magnetic developer unit includes a magnetic developer roller mounted in a housing. Thus, developer unit 34 contains a magnetic roller 40. The roller 40 advances toner particles 45 into contact with the latent image. Appropriate developer biasing is may be accomplished via power supply 42, electrically connected to developer unit 34.

The developer unit 34 develops the charged image areas of the photoconductive surface. This developer unit contains electrically charged magnetic black toner, for example, particles 45 which are moved to the photoconductive surface by the electrostatic field existing between the photoconductive surface and the electrically biased developer roll in the developer unit. Power supply 42 electrically biases the magnetic roll 40. With appropriate biasing applied to the roll 40, the uncharged image areas may be preferentially developed while charged areas are left untoned in a discharge area development mode.

A sheet of support material 54 is moved into contact with the toner image at transfer station D. The sheet of support material is advanced to transfer station D by a suitable sheet feeding apparatus, not shown. Preferably, the sheet feeding apparatus includes a feed roll contacting the uppermost sheet of a stack copy sheets. Feed rolls rotate so as to advance the uppermost sheet from the stack into a chute which directs the advancing sheet of support material into contact with the photoconductive surface of belt 10 in a timed sequence so that the toner powder image developed thereon contacts the advancing sheet of support material at transfer station D.

Transfer station D includes a corona generating device 58 which sprays ions of a suitable polarity onto the backside of sheet 54. This attracts the toner powder image from the belt 10 to sheet 54. After transfer, the sheet continues to move, in the direction of arrow 62, onto a conveyor (not shown) which advances the sheet to fusing station E.

Fusing station E includes a fuser assembly, indicated generally by the reference numeral 64, which permanently affixes the transferred powder image to sheet 54. Preferably, fuser assembly 64 comprises a heated fuser roller 66 and a pressure roller 68. Sheet 54 passes between fuser roller 66 and pressure roller 68 with the toner powder image contacting fuser roller 66. In this manner, the toner powder image is permanently affixed to sheet 54. After fusing, a chute 70 guides the advancing sheet 54 to a catch tray 72 for subsequent removal from the printing machine by the operator. It will also be understood that other post-fusing operations can be included, for example, stapling, binding, inverting and returning the sheet for duplexing and the like.

After the sheet of support material is separated from the photoconductive surface of belt 10, the residual toner particles carried by image and the non-image areas on the photoconductive surface may be charged to a suitable polarity and level by a preclean charging device (not shown) to enable removal therefrom. These particles are removed at cleaning station F. The vacuum assisted, electrostatic, brush cleaner unit is disposed at the cleaner station F. The cleaner unit has a brush roll 74 that rotates at relatively high speeds which creates mechanical forces that tend to sweep the residual toner particles into an air stream (provided by a vacuum source), and then into a waste container. Subsequent to cleaning, a discharge lamp or corona generating device (not shown) dissipates any residual electrostatic charge remaining prior to the charging thereof for the next successive imaging cycle.

It is believed that the foregoing description is sufficient for purposes of the present application to illustrate the general operation of an electrophotographic printing machine which may benefit from the present invention therein.

Figure 6:
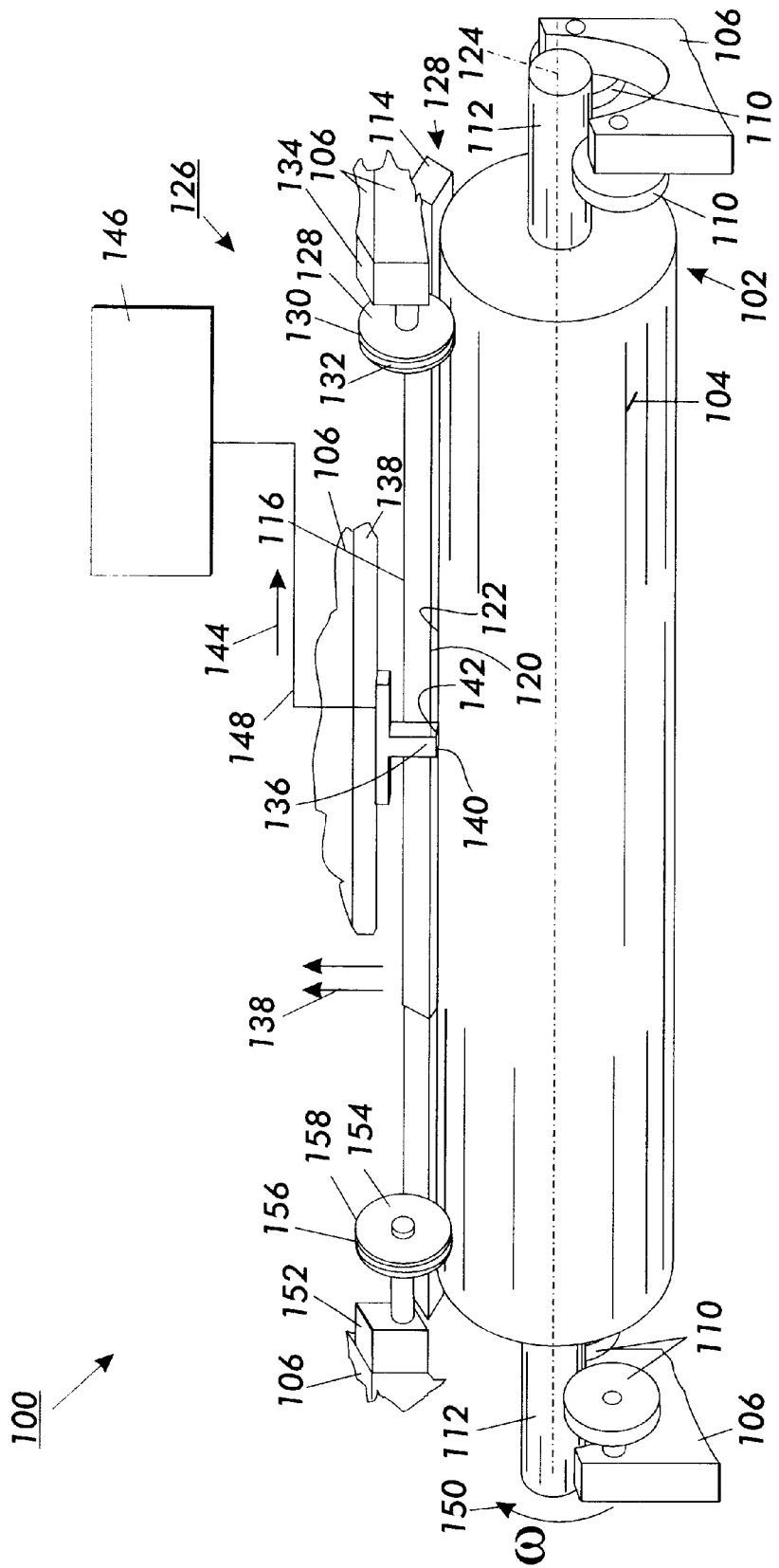
FIG. 6 is a perspective view of a second embodiment of a charge measurement device according to the present invention for use in measuring the charges on a cylindrical member.

According to the present invention, and referring now to FIG. 6, a first embodiment of an apparatus according to the present invention is shown as apparatus 100. Apparatus 100 is utilized to measure the permittivity of a material or workpiece 102 by obtaining measurements of the voltage above a surface 104 of the material 102 after a period of time subsequent to applying a charge to the surface 104 of the material 102.

While the apparatus 100 may be utilized to test the permittivity of any type of workpiece 102, the apparatus 100 is particularly well-suited for measuring the permittivity of an insulative or a semiconductive material, such as materials used for certain type of components used in the printing art, namely photoconductive drums, donor rolls such as those used in hybrid scavengeless development as disclosed in U.S. Pat. No. 4,868,600 to Hayes et al., the relative portions thereof incorporated herein by reference and such as those used in rolls for direct electrostatic printing such as those disclosed in U.S. Pat. No. 4,755,837 to Schmidlin et al., the relative portions thereof incorporated herein by reference.

Electrostatic printing rolls, donor rolls, and photoconductive drums require particularly precise electrical properties. In particular, electrostatic rolls and donor rolls may require a permittivity of a very narrow range for proper operation of the roll. The apparatus 100 is therefore well suited for measuring these particular devices. Furthermore, donor rolls and electrostatic print rolls, due to the manufacturing processes involved in making the rolls, may have electrical properties including permittivity that varies widely within a particular roll. The apparatus 100 may thus be utilized to measure the roll throughout the outer periphery thereof.

The apparatus 100 includes a frame 106. The frame 106 is utilized to support the apparatus 100. The frame 106 may be made of any suitable, durable material capable of supporting the apparatus 100. For example, the frame 106 may be made of a metal or a plastic. If made of a metal, the frame 106 must include portions thereof which are nonelectrically conductive in order to isolate the charged portions of the apparatus from the exterior of the apparatus.

The test piece 102 is rotatably secured to the frame 106. For example, the frame 106 may include supports in the form of a cradle 110 to which, for example, journals 112 extending outwardly from the test piece 102 are rotatably secured. In a preferred embodiment, the surface of the test piece 102 may rest on a cradle formed by small rotatable secured wheels and thus be held at a fixed distance from other peripheral components.

The apparatus 100 further includes a charging device 114 for applying a charge to the test piece 102. The charging device 114 is operably associated with the frame 106. As shown in FIG. 6, the charging device 114 is fixedly mounted to the frame 106. The charging device includes a charging device portion 116 of the charging device 114 is positioned at a first charging position 120 which is proximate to a first material position 122 of the test piece 102. The first material position 122 is located on surface 104 of the test piece 102.

The charge corotron 114 may be any charging device capable of applying a charge to surface 104 of the test piece 102. For example, the charging device 114 may be a wire-type corotron, a pin-type corotron, a glass-coated corotron, a corotron including a screen or a bias charge roller. As shown in FIG. 6, the charging device 114 is in the form of a screen corotron.

In order that the entire length of the test piece 102 has surface 104 charged, preferably, the charging device 114 extends along axis 124, the entire length of surface 104. The charging device 114 may optionally include an adjustment (not shown) for aligning the charging device 114 with the surface 104 such that the surface of the charging device 114 adjacent the surface 114 is parallel with axis 124 such that the distance between the charging device 114 and the surface 104 remain constant along the length of the surface 104 of the test piece 102.

The apparatus 100 further includes a mechanism 126 for rotating the test piece 102. The mechanism 126 is operably associated with the frame 106 and may, as shown in FIG. 6, be mounted to the frame 106. The mechanism 126 may be any mechanism capable of rotating the test piece 102 accurately. For example, the mechanism 126 may be in the form of a direct drive, L-drive, gear drive or any type of mechanical drive capable of rotating the test piece 102 about axis 124. It should be appreciated that the mechanism 126 may be in the form of a mechanism which is secured to one of the journals 112.

Preferably, for simplicity and to provide for a mechanism which is capable of accommodating a variety of range of test pieces with varying lengths and diameters, preferably, the mechanism 126 is in the form of a drive wheel. The drive wheel 126 includes an outer surface 128 thereof, which provides direct contact with the surface 104. The drive wheel 126 thus provides for accurate continuous rotation of the test piece 102 about axis 124. For example, as shown in FIG. 6, the drive wheel 126 includes a groove 130 formed therein. An o-ring 132 is positioned in the groove 130 and provides for the outer surface 128 for driving the test piece 102.

The mechanism 126 may be driven by any suitable driver. For example, the mechanism 126 may be connected through a set of gears, pulleys and belts to a main drive source whereby the mechanism 126 may be rotated. For simplicity and to increase the accuracy of the rotation of the test piece 102, preferably, a motor is directly connected to the drive wheel 126 to drive the drive wheel 126. It should be appreciated that similarly the motor 134 may be positioned on an axis spaced from that of the drive wheel 126 with o-ring 132 interconnecting the motor 134 to the drive wheel 126.

The motor 134 may be any suitable motor capable of providing accurate rotation of a test piece 124. Preferably, the motor 134 is a positioning-type motor so that the motion of the motor 134 may be accurately controlled. It should be appreciated however, that a less complicated and sophisticated motor may be used in conjunction with a separate positioning detector operably associated with the test piece 102 and including feedback with the motor 134 so that the movement of the test piece 102 can be accurately controlled with a less expensive motor. Preferably, however, the motor 134 is an accurate positioning-type motor.

For example, the motor 134 is preferably a stepper motor. To provide for an apparatus 100 which can accommodate different rotational speeds of the test piece 102, preferably, the motor 134 is a variable speed motor. For example, as shown in FIG. 6, the motor 134 is in the form of a variable speed stepper motor.

The apparatus 100 further includes a measuring device 136 which is operably associated with the frame 106. The measuring device is preferably in the form of a voltage measuring device, although other measuring devices capable of measuring an electrical field 138 emanating from the test piece 102 may be considered for use with this invention. The voltage measuring device 136 may be directly mounted to the frame 106 or, preferably, as shown in FIG. 6, may be mounted to a slide 138. The slide 138 is slidably mounted to the frame 106. The slide 138 provides for positioning of the voltage measuring device 136 along the entire length of the surface 104 in the direction parallel to axis 124.

The voltage measuring device 136 is utilized for measuring an electrical field 138 emanating form the test piece 102, thus indicating the charge residing on the test piece 102. The voltage measuring device 136 includes a measuring device portion 140 of the voltage measuring device 136 positioned proximate to a second material position 142 on the external periphery 104 of the test piece 102. The second material position 142 is spaced from the first material position 122.

The voltage measuring device 136 may be any device capable of measuring the electrical field 138 emanating from the test piece 102. For example, the voltage measuring device 136 may be in the form of a transducer for converting the electrical field 138 into an electrical signal 144 which corresponds to the electrical field 138. For example, the transducer 144 may be in the form of a noncontact voltage probe including a measuring device portion 140 positioned adjacent the surface 104. The noncontact voltage probe 136 may be, for example as shown in FIG. 6, in the form of an electrostatic voltmeter. The electrostatic voltmeter 136 is operably associated with the test piece 102 for receiving the electrical field 138 emanating from the test piece 102 and for transmitting the signal 144 corresponding to the electrical field 138.

The voltage measuring device 136 preferably further includes a displaying device 146 for displaying the signal 144. The displaying device 146 may be any device capable of displaying an indication of the electrical field 138. For example, the displaying device 146 may be a simple strip recorder, a meter, or preferably be in the form of a data recorder which may cooperate with a computer to provide for a display of the electrical field 138.

The apparatus 100 further preferably includes an electrical conduit 148 positioned between the voltage measuring device 136 and the displaying device 146. The conduit 148 is utilized for transmitting the signal 144 from the transducer 136 to the displaying device 146. The electrical conduit 148 may be in any form, but typically is in the form of an electrical cable.

The drive wheel 126 cooperates with the test piece 102 to rotate the test piece 102 to a position proximate the measuring device portion 104 of the voltage measuring device 136 in a first time period. The voltage measuring device 136 is adapted to measure a remaining charge at the first material position 122 after the test piece 102 is so rotated in the direction of arrow 150. The first time period and the remaining charge are utilized to determine the permittivity of the test piece 102.

Preferably, the apparatus 100 further includes a test piece surface displacement measuring device 152. The measuring device 152 is associated with the surface 104 of the test piece 102 and is utilized for accurately measuring the rotation of the test piece 102. While any device capable of accurately measuring the movement of the surface 104 of the test piece 102 may be utilized as the surface measuring device 152, preferably, the measuring device 152 is in the form of a rotary encoder. The rotary encoder is in contact with an encoder drive wheel 154. The drive wheel 154 includes, for example, an o-ring 156 which is fitted into a groove 158 within the drive wheel 154. The o-ring 156 contacts the surface 104 of the test piece thereby causing the drive wheel 154 to rotate. The drive wheel 154 is operably connected to the rotary encoder for determining the motion of the surface 104 of the test piece 102.

While, as shown in FIG. 6, the drive wheel 154 is directly connected to the rotary encoder 152, it should be appreciated that the drive wheel 154 and the rotary encoder 156 may be positioned on parallel spaced-apart shafts and the drive wheel and the rotary encoder being interconnected by an o-ring not shown interconnecting the drive wheel to the rotary encoder 152.

The apparatus 100 is utilized to measure the permittivity of the test piece 102 by first placing the test piece 102 in the apparatus 100 and energizing the apparatus 100. The motor 134 causes the test piece 102 to rotate. The screen corotron 114 is likewise energized to create an electrical ion stream onto the test piece 102. Also, the voltage measuring device 136 is energized in order that the electrical field 138 from the test piece 102 may be measured. The permittivity of the test piece 102 is determined by following a series of steps. First, a first charge is applied to first material position 122 in alignment with the charging device 114.

The apparatus 100 can be utilized in at least two different distinct ways or methods to measure the permittivity of the test piece 102. In the first of these methods, the test piece 102 is rotated measuring the electric field 138 by using the voltage measuring device 136 from a point when the test piece 102 is not charged and the electrical field 138 is approximately zero and then having the charging device 114 energized. The test piece 102 is continually rotated while the charging device 114 is energized until the test piece 102 is saturated, i.e., until the electrical field 138 within the test piece 102 becomes a constant.

The mathematical slope of the charge to voltage curve and the length of time for the test piece to obtain a full charge is thus an indication of the permittivity of the test piece 102 combined with its intrinsic resistive or ionic loss mechanisms.

Alternatively, the permittivity of the test piece may be obtained by first rotating the test piece 102 with the charging device 114 until the electrical field 138 remains constant, i.e., until the test piece 102 is fully charged. While the test piece 102 is being charged, the voltage measuring device 136 may be utilized to measure the charge as a function of time from the electrical field 138 of the test piece 102 until the electrical field 138 is saturated. The rate of charge acceptance is an indication of the permittivity of the test piece 102.

The dielectric loss mechanisms of the test piece 102 may also be obtained. The apparatus 100 is energized which includes having the motor 134 energized to begin the rotation of the test piece 102 about the journals 112. The charge corotron 114 is energized. The test piece 102 continues to rotate until the electrical field 138 obtains a maximum or steady state value. That maximum or steady state value is then measured. The charge corotron 114 is deenergized.

The workpiece is then rotated a first number of revolutions. A first time is then measured which is equal to the time for the first material to rotate the first number of revolutions. After rotating the first number of revolutions, the electrical field 138 remaining on the first position on the surface 104 of the test piece 102 after rotating the test piece the first number of revolutions is measured.

The test piece is then rotated a further second number of revolutions. A second time is measured which is required for rotating the test piece the second number of revolutions. A second charge remaining on the first material position 122 on the surface 104 of the test piece 102 after rotating the test piece 102 the second number of revolutions. The dielectric charge loss rate of the test piece is then calculated based on the first time required, the first charge remaining, the second time required and the second charge remaining.

One of the problems in obtaining and determining quality donor rolls and electrostatic print rolls is that the permittivity of these rolls varies within a particular roll. Therefore, it is advantageous to measure or sample the permittivity at a large number of locations on the periphery of the rolls. The apparatus 100 permits such measurement at several points on the surface 104 of the test piece 102. The ability to test many locations on the surface 104 is made possible by the ability of the charge measuring device 136 to take continuous measurements of the electrical field 138 as the test piece 102 is rotated. This permits a testing of an infinite number of points along a circular band on the surface 104.

Further, since the charge measuring device 136 is preferably located on slide 138 that moves in a direction parallel to axis 124, a infinite number of circular bands along the periphery may be measured by moving the slide 138 along the axis 124 thereby permitting measurements of virtually the entire surface 104 of the apparatus 100. By averaging the readings of the electrical field by the charge measuring device along different locations on the surface 104, an accurate average measurement of the permittivity of the apparatus is possible with the apparatus 100.

Since the motor 134 is preferably a variable speed motor, the rotational speed ω in the direction of arrow 150 of the rotating test piece 102 may be varied to accommodate test pieces which lose their charge very quickly as well as those who lose their charge much more slowly. As should be appreciated, the test pieces which lose their charge very slowly may be rotated at a speed ω which is quite slow, say for example, 10 rpm. Further, for those test pieces which lose their charge much more quickly, the test piece may be rotated at a much higher speed, say for example 400 or 500 rpm. The applicants have found that a speed ω of around 200 rpm is satisfactory for most test pieces.

Figure 1:
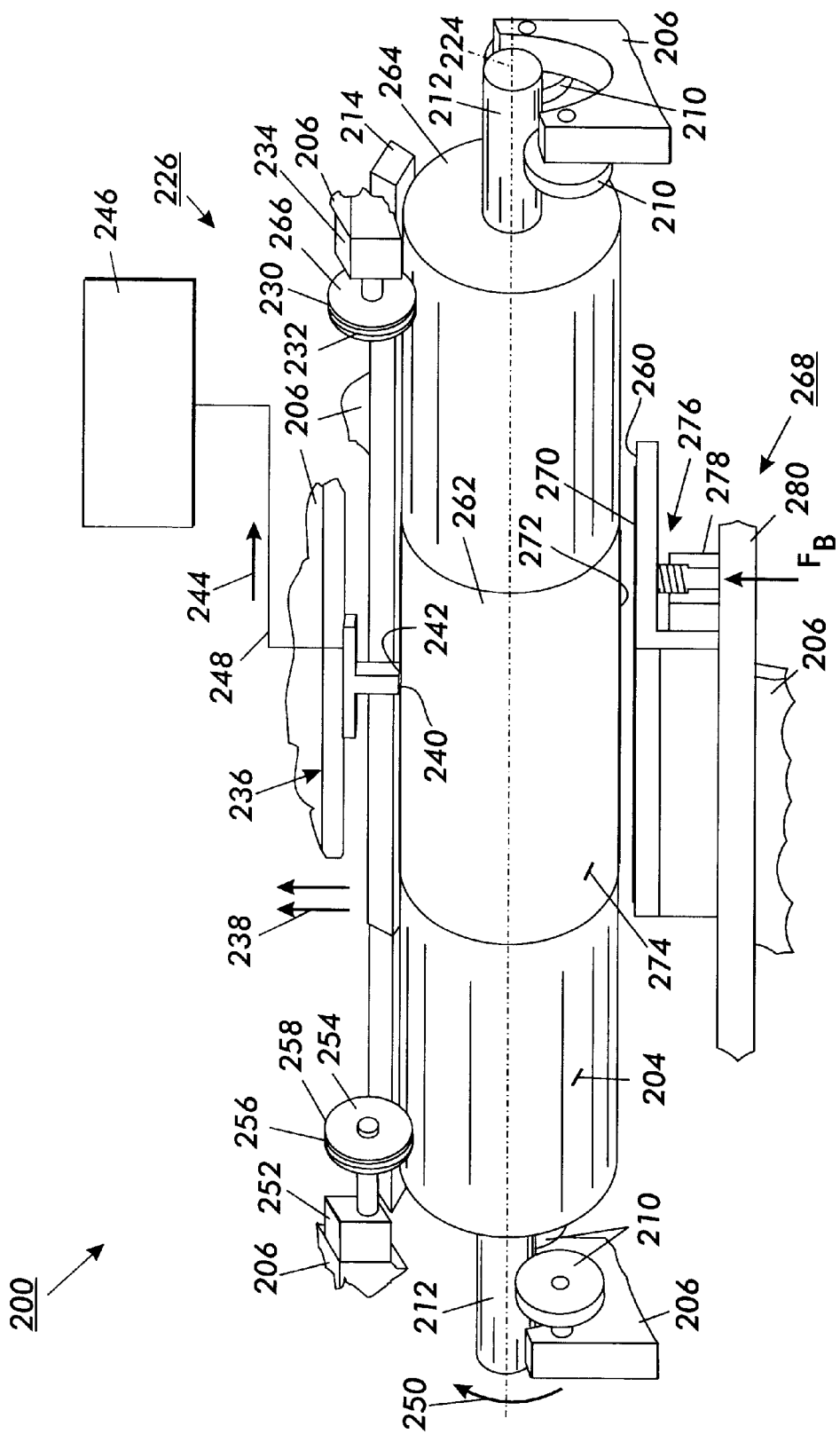
FIG. 1 is a perspective view of a first embodiment of a charge measurement device according to the present invention for use in measuring the charges on a flexible material.

Referring now to FIG. 1, an alternate embodiment of the present invention is shown as apparatus 200 for measuring the tribocharge built up on toner image receiving materials, such as paper, film, plastic labels and similar materials. The build up of static electricity on machine components and receiver sheet paper moving through copiers and printers is a significant cause of paper handling problems. The apparatus 200 is used for measuring a triboelectric charge 238 applied by material or component 260 to a flexible sheet 262.

One important aspect of the present invention is the ability to relate the measured charge on a test piece due to charges placed by a corona charging device to those charges placed by tribocharging the test piece against any machine component. Thus, even with losses and speed variations, a direct calibration of amount of charge can be made.

The apparatus 200 includes a frame 206 for supporting the apparatus 200. The frame 206 may be similar to frame 106 of apparatus 100. The frame 206 may be made of any suitable, durable material and may be made of a metal. If made of a metal, the frame 206 preferably includes insulative portions (not shown) which separate the internal portions with the external portions of the frame such that any electrical charges do not reach the outer portion of the frame 206.

The apparatus 200 further includes a mounting device 264 for mounting the sheet 262 to external periphery 204 of the mounting device 264. The mounting device 264 is rotatably mounted to the frame 206. For simplicity and as shown in FIG. 1, the mounting device 264 is in the form of a cylindrical drum. Preferably, the drum 264 is made of an electrically conductive material. For example, the drum 264 may be made of aluminum. While, as shown in FIG. 1, the paper 264 may be secured directly to the surface 204 of the drum 264. It should be appreciated that a layer of a different material may be placed between the sheet 262 and the surface 204 of the drum 264. For example, a sheet of a strong polyester film such as Mylar™, a trademark of Imperial Chemical Industries, plc. (not shown) may be placed between the sheet 264 and the surface 204.

The Mylar™ may be utilized to limit the flow of electrical charge between the sheet 262 and the drum 264. The use of the Mylar™ may be particularly advantageous if the sheet 262 is sufficiently conductive that the flow of electrical charge from the sheet 262 and the drum 264 may interfere with the measuring of the triboelectric charge 238 on the sheet 262.

Preferably, as shown in FIG. 1, the drum 264 is rotatably mounted to the frame 206. The drum 264 may be mounted to the frame in any suitable fashion. For example, as shown in FIG. 1 journals 212 may extend outwardly from the drum 264 and be supported in cradle supports 210 which are mounted to the frame 206. Preferably, if the drum is made of an electrically conductive material, the drum is preferably electrically insulated from at least a portion of the frame 206. For example, insulative material may be placed somewhere within the frame to prevent an electrical field from reaching the outer periphery of the frame 206.

The apparatus 200 further includes a driving mechanism 226 for rotating the drum 264. The driving mechanism 226 may be any mechanism capable of rotating the drum 264 and may, for example, include a motor 234 for providing rotation for the driving mechanism 226. The driving mechanism 226 is operably associated with the drum 264 and, as shown in FIG. 1, may include a drive wheel 266 which is connected to the motor 234. While it should be appreciated that the drive mechanism 226 may be operably connected to the drum 264 in any suitable fashion such as by gears or other drives which would connect the drive mechanism 226 through the journal 212 to the drum 264. But, preferably, as shown in FIG. 1, for simplicity and to provide for an accurate drive to the surface 206 of the drum 264 and to provide for a multitude of drum diameters, the driving mechanism 226 includes the drive wheel 266.

The drive wheel 266 may have any suitable form capable of driving the surface 204 of the drum 264. For example, as shown in FIG. 1, the drive wheel 266 includes an o-ring 232 adapted for contact with the surface 206. The o-ring 232 is preferably fitted in a groove 232 in the outer portion of the drive wheel 266. The motor 234 may for simplicity be mounted to frame 206.

The apparatus 200 further includes a support 268 for supporting the paper contacting component 260. The sheet contacting component 260 may be any material for which the triboelectric charge generated when in contact with the flexible sheet 262 is desired to be determined. Typically, such paper contacting components are those components which contact the flexible sheet or paper as it passes through a, for example, printing machine. Such components 260 include metal baffles, plastic baffles, plastic and metal rolls, Teflon blades or any component which contacts the flexible sheet in a printing machine (e.g. Reference numerals 54, 58, 66, 68, 70 and 72 of FIG. 5).

The support 268 may be any support capable of supporting the component 260. For example, as shown in FIG. 1, the support 268 may be in the form of a plate to which the component 260 may be secured. The component 260 may be secured to the support 268 in any suitable fashion, such as by fasteners, glue, or by clamps. The support 268 is preferably positioned adjacent the sheet 262 mounted on the drum 264. The support 268 is positioned such that the component 260 and the sheet 262 are in intimate contact with each other as the drum 264 is rotated such that the component 260 and the sheet 262 form a triboelectric charge on external surface 274 of the sheet 262. The component 260 includes a component portion 270 which is in intimate contact with the sheet 262 at a first position 270 on external periphery 274 of the sheet 262.

Preferably, as shown in FIG. 1, the support 268 further includes a biasing device 276 for biasing the component 260 against the sheet 262 with a force $F_B$ normal to the drum 264. The biasing device 276 may have any suitable form and may be in the form of a cantilevered beam or a leaf spring as shown in FIG. 1. In order that the force $F_B$ may be varied to determine the effect of the normal force $F_B$ on the generation of the triboelectric charge, preferably, the biasing device 276 further includes a tensioning device 278 for adjusting the biasing force $F_B$. The tensioning device 278 may be any device capable of adjusting the bias device 276. For example, the tensioning device 278 may be in the form of a adjustment screw which urges the biasing device 276 further toward the sheet 262.

While the invention may be practiced with the support 268 fixedly mounted on the frame 206, preferably, so that the entire paper surface 262 may be subjected to the triboelectric charged 238. The support 268 is preferably, as shown in FIG. 1, mounted on a slide 280 for permitting motion of the support 268 in a direction parallel to axis 224 of the drum 264. The slide 270 permits the component 260 if it is less than the width of the paper 262 to be moved along axis 224 so that the entire width of the paper 262 is in contact with the component 260. The slide 280 may have any suitable form and shape capable of moving the support 268 along an axis parallel to axis 224. As shown in FIG. 1, the slide 280 is mounted to frame 206.

The apparatus 200 further includes a charge measuring device 236 which is operably associated with the drum 264. The charge measuring device 236 is utilized to measure the triboelectric charge 238 residing on the sheet 262. The charge measuring device 236 includes a measuring device portion 240 of the measuring device 236 which is positioned proximate to a second sheet position 242 on the surface 274 of the sheet 262. The second sheet position 242 is spaced from the first sheet position 272.

The charge measuring device 236 may be any device capable of measuring triboelectric charge on a surface. For example, the charge measuring device may be in the form of a transducer. The transducer 236 is operably associated with the drum 236 and is utilized to receive the triboelectric charge 238 emanating from the sheet 262 and for transmitting a signal 244 corresponding to the triboelectric charge 238. The apparatus 200 may further include a displaying device 246 for displaying the signal 244 sent from the transducer 236. The apparatus 200 may further include an electrical conduit 248 for transmitting the signal 244 from the transducer 236 to the displaying device 246.

The displaying device 246 may be any device capable of displaying a signal indicative of the triboelectric charge 238. For example, the displaying device 246 may be in the form of a strip chart or may be in the form of a data recorder which may be used in conjunction with a portable computer to display information corresponding to the triboelectric charge 238.

The driving mechanism 226 cooperates with the sheet 262 to rotate the first sheet position 272 in the direction of arrow 250 to the second sheet position 242 proximate the measuring device portion 240 of the charge measuring device 236 in a first time period. The charge measuring device 236 then obtains a measurement of the triboelectric charge 238 on the sheet 262 at that first time period. The remaining charge at position 242 is utilized to measure the triboelectric charge applied by the material to the sheet at position 272.

Preferably, continual measurements are made by the charge measuring device 236 as the sheet 262 continues to rotate in the direction of arrow 250. After a number of rotations in the direction of arrow 250, the triboelectric charge 238 measured at the transducer 236 will reach a maximum or steady state condition at which the triboelectric charge generated by the component 260 rubbing against the sheet 262 equals the charge loss rate to the ground plate of the system.

To eliminate any residual triboelectric charge 238 that may have accumulated on a sheet 262 prior to a test for triboelectric charge and to permit the repeating a measurement without removing the sheet from the drum 264, preferably, the apparatus 200 further includes a charging device 214. The device 214 maybe used to neutralize or remove the triboelectric charge 238 from the drum 264 and the sheet 262. The charging device 214 may be any device capable of providing a charge to the sheet 262 and the device 264.

Preferably, the charging device 214 is in the form of a noncontact charging device although the use of a biased charge roll may be feasible for the practice of the invention. The charging device 214 may be any type of corona generating device, for example, a corotron, a glass coated corotron, a pin-type scorotron, or a screened corotron or scorotron.

Preferably, the charging device 214 is in the form of a screen corotron. The charging device 214 is positioned adjacent to and spaced from the drum 264 and the sheet 262. Preferably, the charging device 214 extends in a direction parallel to axis 224 along the entire length of the drum 264.

Figure 2:
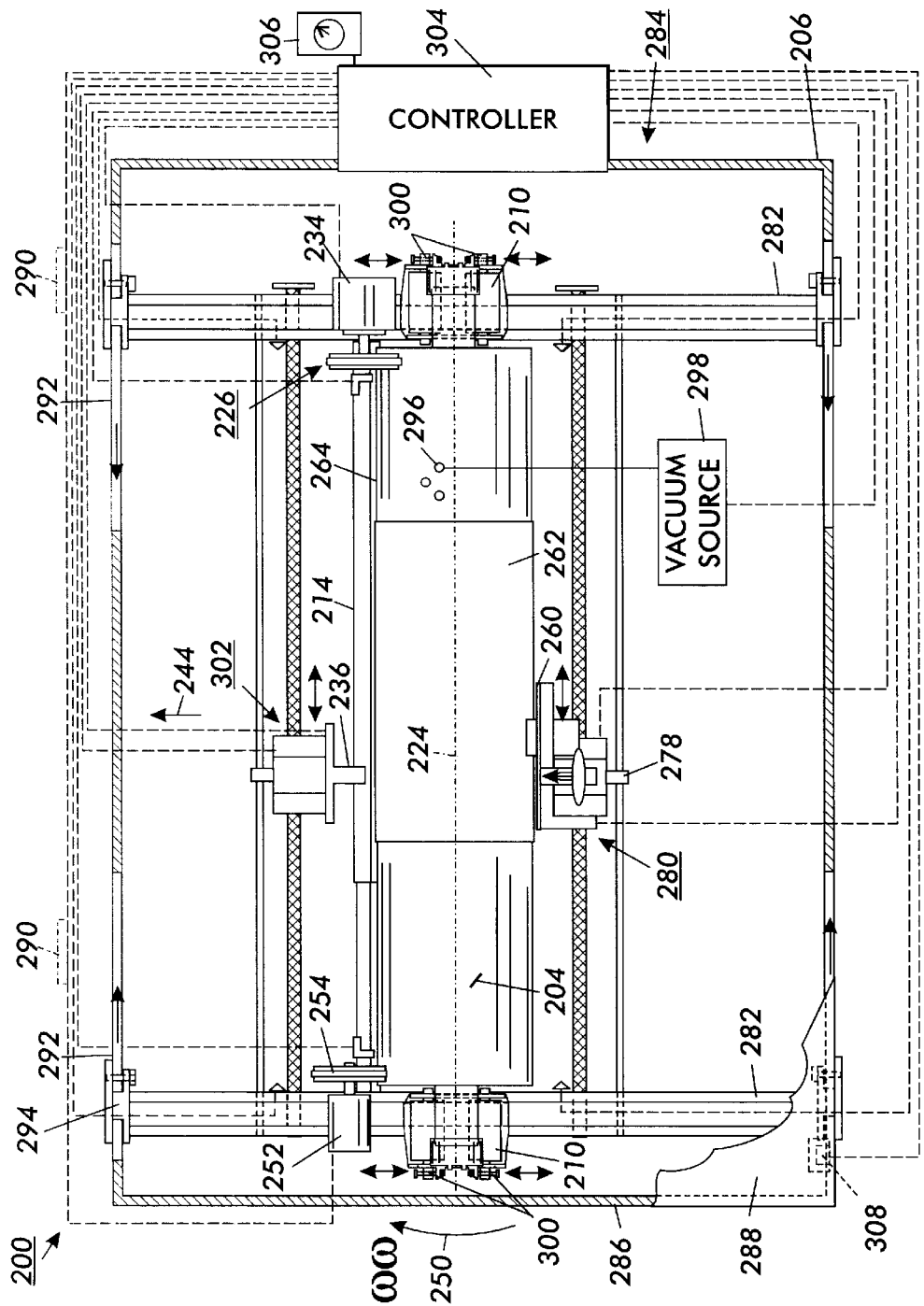
FIG. 2 is a top view of the charge measurement device of FIG. 1 shown in greater detail.

Referring now to FIG. 2, the apparatus 200 is shown in greater detail. As shown in FIG. 2, the frame 206 includes internal portions 282 to which the cradle supports 210 are mounted. As shown in FIG. 2, the internal portions 282 may be in the form of a pair of spaced-apart rails. The frame 206 further includes a shell or housing 284.

As shown in FIG. 2, the housing 284 is in the form of a box including a fixed lower portion 286 and a cover 288 which is secured to the lower portion 286 by, for example, hinges 290. To accommodate different lengths of drums, preferably, the rails 282 are adjustable along axis 224 by adjustments 292 in the form of, for example, slots formed in the housing 284. To isolate the rails 282 from the housing 284, preferably, insulated blocks of, for example, a thermosetting plastic having high chemical and electrical resistivity such as Bakelite™, a trademark of B. P. Chemicals, Ltd., or a similar insulator are positioned between the rails 282 and the frame 284.

While it should be appreciated that the invention may be practiced with the sheet 262 merely laid upon the drum 264, preferably, the sheet 262 is fixedly secured to the drum 264. The sheet 262 may be secured to the drum 264 in any suitable manner such as by fasteners or glue. Preferably, however, for ease and simplicity and to have minimal effect on the measurements of the triboelectric charge 238, the sheet 262 is taped to the drum 264 by electrically conductive tape. Alternatively, and equally as preferred, the sheet 262 is secured to the drum 264 by a series of openings 296 which are connected to a vacuum source 298 to provide a vacuum holding force for the sheet 262 against the drum 264.

Preferably, as shown in FIG. 2, the apparatus 200 further includes an alignment device 300 for aligning the charging device 236 to the sheet 262. For example, as shown in 262, the alignment device 300 may be in the form of adjustment screws located on the rails 210 for adjusting the position of the journals 212 with respect to the rails 282 such that the drum 264 may be aligned with the charging device 236.

While it should be appreciated that the invention may be practiced with any motor 234 for driving the driving mechanism 226, the more accurate the rotating of the drum 264, the more accurate the measurements from the apparatus 200 will become. Thus, while any motor 234 may be utilized, preferably, the motor 234 is in the form of a positioning motor, for example, a stepper motor.

Referring again to FIG. 1, alternatively, the accurate rotation of the drum 264 may be further enabled by the use of a movement detector 252 in the form of, for example, a rotary encoder. The rotary encoder 252 is utilized to measure the position of the surface 204 of the drum 264. A drive wheel 254 may be connected to the rotary encoder 252 for contact by an o-ring 256 positioned in groove 258 for rolling contact with the surface 204.

Referring again to FIG. 2, while it should be appreciated that the invention may be practiced with a charge measuring device 236 that is fixedly positioned on the frame 206, preferably, the transducer 236 is mounted on a slide 302 for permitting movement in a direction parallel to axis 224. The use of the slide 302 permits the transducer 236 to measure the triboelectric charge along the entire length of the sheet 262. The electrical properties within the sheet 262 may vary along the length of the sheet. Further, the component 260 may not extend the full length of the sheet and as such the triboelectric charge within the sheet 262 may have a non-uniform pattern.

The apparatus 200 may be utilized to measure a particular point on the sheet 262 or with the rotation of the drum 264 in the direction of arrow 250 be capable of measuring a circle or band of positions on the sheet 262. Further, by movement of the slide 302, the transducer 236 can measure the triboelectric charge on the entire surface of the sheet 262. Further by adjusting the tensioning device 278, the triboelectric charge based upon the severity of the contact between the component 260 and the sheet 262 may be determined.

Furthermore, the motor 234 may be of variable speed and motor such that the rotational speed ωω of the drum 264 may be varied. The varying of the speed of rotation of the drum 264 may be used to simulate the speed of the sheet 262 through the paper path of the printing machine. Therefore, the adjustment of the speed of the motor 234 is valuable to simulate actual conditions within a printing machine.

Preferably, as shown in FIG. 2, the apparatus 200 further includes a controller 304 for controlling the apparatus 200. The controller 200 may be quite simple and merely be used to receive the signal 244 from the transducer 236 to obtain measurements of the triboelectric charge 238. Preferably, however, the controller 304 may be utilized to control all the movable and adjustable components within the apparatus 200.

For example, the controller 304 may be electrically connected to any or all of the, rotary encoder 252, transducer slide 302, support slide 280, tension device 278, vacuum source 298, motor 234, and transducer 236. It should be appreciated that the controller 304 may be utilized to establish any type of complex test on the sheet 262 which may be used to check a spot, a band or any portion of the sheet 262.

In fact, the controller 304 may be connected to a timer 306 which may permit the determination of the charge rate, the loss rate, and the period of time at which a steady state or maximum triboelectric charge 238 accumulates between the component 260 and the sheet 262. The controller 300 may also be electrically connected to safety devices such as limit switches 308 which may, for example, prevent the operation of the machine with the housing 284 open.

The apparatus 200 may be utilized to measure the triboelectric charge applied to the flexible sheet 262 by the material 260. The method may include the steps of rotatably mounting the drum 264 to the frame 206. The sheet 262 is then mounted to the surface 204 of the drum 264. A support 268 is also mounted to the frame 206. The material or component 260 to be tested is mounted to the support 268 and placed in intimate contact with the sheet 262 on the drum 264. The drum 264 is then rotated about the frame 206 with the sheet 262 and the component 260 having relative motion therebetween. The triboelectric charge 238 applied to the surface 274 of the sheet 262 by the rubbing of the sheet 262 with the component 260 is then measured.

Referring now to FIG. 3, a series of tests were performed on various sheets of paper placed upon the drum of the apparatus 200 of FIG. 1. The transducer 236 was utilized to measure the triboelectric charge 238 generated by the paper sample mounted on the drum and in contact with the same sheet of paper and with the sheet on the drum in contact with a Teflon blade on the support 268. Voltages were measured by the transducer 236 and are shown on the table in FIG. 3.

It is readily apparent by reviewing the information on FIG. 3, that the triboelectric charge generated by paper varies widely from one type of paper to another. It is also readily apparent that the contact of various types of paper against a common component will result in very different triboelectric charge accumulation. Thus, it should be readily apparent that by utilization of the present invention, various materials may be tested and those which provide the appropriate level of triboelectric charge may be selected when designing printing machines.

Figure 4:
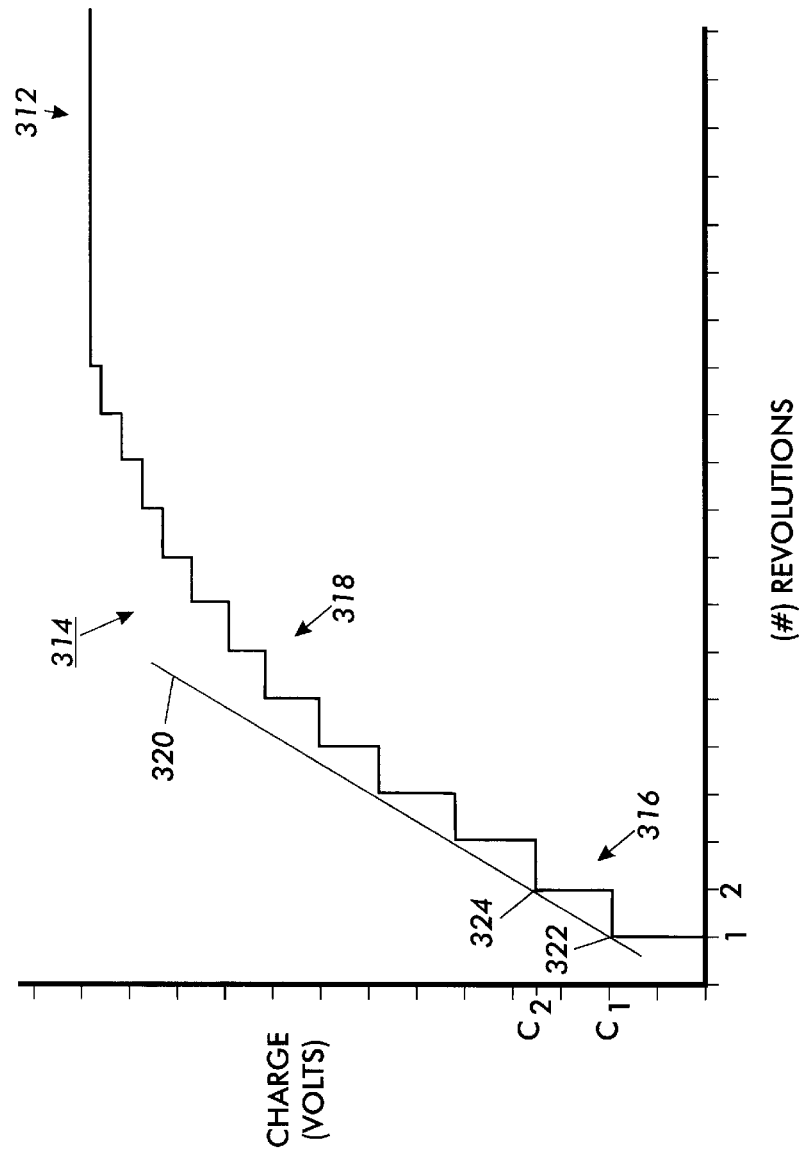
FIG. 4 is a plot of voltage versus revolutions for a substrate in contact with another material utilizing the charge measurement device of FIG. 1.

Referring now to FIG. 4, voltage measured by the transducer is plotted on a graph with respect to time. Time is represented by the revolutions of the drum of the apparatus. The curve 314 represents the voltage on the surface of the drum with respect to time. The curve 314 has three portions: a first portion 316 which is almost linear starting at zero volts, a third portion 312 which is linear and which represents the maximum voltage that may be retained by the surface of the drum with the given power of the charging device, and a second portion 318 which is curved positioned between the first portion 316 and the third portion 312.

The first portion 316 represent the portion of the curve in which the surface charge losses are minimal. The surface charge losses include resistive losses as well as dielectric losses. The surface charge losses cause the amount of charge on the external periphery of the member to be reduced.

Permittivity may be described as the slope of the curve 314 in the first portion. The permittivity may be described by the formula:

$$C = K \times T / \epsilon$$

where:

$\epsilon$ = permittivity

C = charge absorbed by the surface being charged in volts

T = cycle time in which charge device charges at a fixed rate (charge/time)

K = device constant based on charger width and power and drum thickness

The permittivity is thus described by the slope of the line 320 through the first portion 316 of the curve 314.

If the apparatus 200 is utilized to determine charge C1 and charge C2 and if these charges C1 and C2 are plotted as points 322 and 324, a line may placed therebetween (320) which is used to determine the permittivity of the material.

The second portion 318 of the curve 314 represented the portion of the curve where the surface charge losses begin to become substantial. The surface charge losses include resistive losses as well as dielectric losses. The surface charge losses cause the amount of charge on the external periphery of the member to be reduced. A more complicated equation may be theoretically or empirically determined to represent this portion of the curve if the surface charge losses are included in the analysis.

The third portion 318 of the curve 314 represented the portion of the curve defining the maximum voltage that may be retained by the surface of the drum with the given power of the charging device. At the third portion the amount of charge applied by the charging device and the surface charge losses become equal.

The surface charge losses include resistive losses as well as dielectric losses. The surface charge losses cause the amount of charge on the external periphery of the member to be reduced. It should be readily apparent that after a number of revolutions, the charge retained at the external periphery of the drum reaches a steady state as shown by zone 312 within curve 314.

By providing an apparatus for accurately measuring the permittivity of a semiconductive material, inspection of the quality of a semiconductive roll may be improved.

By providing an apparatus for measuring the entire periphery of a semiconductive roll, the effectiveness, uniformity, and suitability of a semiconductive roll may be readily determined.

By providing an apparatus for measuring a semiconductive roll including a charging device, a uniform charge may be applied to the semiconductive drum.

By providing an apparatus for measuring a semiconductive roll including a transducer which is slidably positioned along the length of the roll, the entire length of the roll may be measured.

By providing an apparatus for measuring the permittivity of a semiconductive roll including a motor for rotating the roll, the permittivity of the entire circumference of the roll may be measured.

By providing an apparatus for measuring the triboelectric charge of a material against a flexible sheet, the designing of paper paths and paper path components may be optimized to minimize static electricity.

By providing an apparatus that can measure both permittivity and tribocharging on the same substrate, an absolute determination of the tribocharge and loss levels can be obtained.

By providing an apparatus for measuring the triboelectric charge generated between a material and a sheet of paper, better paper handling may be accomplished in the designing of a machine by predetermining the triboelectric effects of components within the paper path.

By providing an apparatus for measuring the triboelectric charge of a sheet rubbing against a material, coatings and components for paper may be selected to minimize triboelectric charge and resulting static electricity.

By providing an apparatus for measuring the triboelectric charge on a sheet which includes a transducer which is movable along the entire length of the sheet, the charge along the entire length of the sheet may be measured.

By providing an apparatus for measuring the triboelectric charge on a sheet which includes a motor for rotating the sheet, the entire circumference of the sheet may be measured.

By providing an apparatus for measuring the triboelectric charge on a sheet including a rotating drum and a translating transducer which is movable along the length of the drum, the entire surface of a sheet may be measured.

By providing an apparatus for measuring the triboelectric charge generated between a component and a sheet including a support for contacting the component against a sheet mounted to a cylindrical drum, an accurate reproducible testing of the triboelectric charge is generated by a paper as it passes a component in a printing machine may be accomplished.

By providing an apparatus for measuring the triboelectric charge generated by a sheet against a component including a charging device to neutralize the sheet, a measurement of the triboelectric charge of a sheet in a paper path may be repeated as often as necessary.

It is, therefore, apparent that there has been provided in accordance with the present invention, an apparatus and a method for measuring charging that fully satisfies the aims and advantages hereinbefore set forth. While this invention has been described in conjunction with specific embodiments, it is evident that many alternatives, modifications, and variations will be apparent to those skilled in the art. Accordingly, it is intended to embrace all such alternatives, modifications and variations that fall within the spirit and broad scope of the appended claims.

We claim:

1. A testing apparatus comprising:

a frame, a member rotatably secured to said frame;

a charging device for applying the charge to the member, said charging device including a charging device portion thereof positioned proximate to an external periphery of the member;

a mechanism for rotating the member, said mechanism operably associated with said frame; and a charge measuring device operably associated with a support for measuring an electrical field emanating from the member, said charge measuring device including a measuring device portion thereof adapted to be positioned proximate to at least one measured position, on said external periphery of the member, said mechanism cooperating with said member to rotate the member, the charge measuring device adapted to measure the charge as a function of time at the at least one measured position;

wherein the testing apparatus measures at least one electrical property including permittivity associated with the member.

2. An apparatus according to claim 1, wherein said charge measuring device comprises an electrostatic voltmeter.

3. An apparatus according to claim 1, further comprising a mechanism for movably positioning the charge measuring device along a direction parallel to an axis of rotation of the member.

4. An apparatus according to claim 1, further comprising a controller for controlling at least one of said charging device, said mechanism and said charge measuring device.

5. An apparatus according to claim 1, wherein said charging device comprises a corotron.

6. An apparatus according to claim 1 wherein said charge measuring device comprises:

a transducer operably associated with a drum for receiving an electrical field emanating from the member and for transmitting a signal corresponding to said electrical field.

7. An apparatus according to claim 6, further comprising:

a displaying device for displaying said signal; and an electrical conduit for transmitting said signal from said transducer to said displaying device.

8. An apparatus according to claim 1, wherein said charging device comprises a material secured to said frame, said material being in intimate contact with said member, said member and said material creating a triboelectric charge.

9. An apparatus according to claim 8, further comprising a holder operably associated with said frame for holding said material.

10. An apparatus according to claim 1, further comprising a support rotatablym mounted to said frame, said support for supoporting the member.

11. An apparatus according to claim 10, further comprising a mechanism for rotating said support, said mechanism operably associated with said support.

12. An apparatus according to claim 7:

wherein said member comprises a sheet of paper;

wherein said support comprises an electrically conductive drum; and wherein said drum is electrically insulated from the frame.

13. An apparatus according to claim 1, wherein the measurements of the voltage charge on the surface of the member are utilized to obtain a measurement of the permittivity of the member.

14. An apparatus according to claim 13, wherein the measurement of the permittivity of the member is obtained by obtaining a first voltage measurement of the measured position, rotating the member for an elapsed time defining at least one complete revolution of the member, obtaining a second voltage measurement of the measured position, and utilizing the first voltage measurement, the second voltage measurement, and the elapsed time.

15. An apparatus according to claim 1, further comprising a position measuring device operably associated with the material for accurately measuring the rotation of the material.

16. An apparatus according to claim 15, wherein said position measuring device comprises a rotary encoder.

17. A testing apparatus for measuring the permittivity of a member comprising:

a frame, the member being rotatably secured to said frame;

a charging device for applying the charge to the member, said charging device including a charging device portion thereof positioned proximate to an external periphery of the member;

a mechanism for rotating the member, said mechanism operably associated with said frame; and a charge measuring device operably associated with a support for measuring an electrical field emanating from the member, said charge measuring device including a measuring device portion thereof positioned proximate to a measured position on an external periphery of the member, a position measuring device operably associated with the member for accurately measuring the rotation of the member; and a controller for controlling at least one of said charging device, said mechanisms and said charge measuring device, said mechanism cooperating with said member to rotate the member to a position proximate the measuring device portion of said charge measuring device, the measurement of the permittivity of the member obtained by obtaining a first voltage measurement of the measured position, rotating the member for an elapsed time defining at least one complete revolution of the member, obtaining a second voltage measurement of the measured position, and utilizing the first voltage measurement, the second voltage measurement, and the elapsed time.

18. A method for measuring the permittivity of a member, said method comprising the steps of:

applying a charge to a first position on a periphery of the member;

rotating the member;

measuring a first voltage charge on the first position on the periphery of the member after rotating the member;

rotating the member a number of revolutions;

measuring a time required for rotating the member the number of revolutions;

measuring a second voltage charge on the first position on the periphery of the member after rotating the member the number of revolutions; and calculating the permittivity of the member based on the time required, the first voltage charge, and the second voltage charge.

19. The method as in claim 18:

wherein the step of applying a charge to a first position on a periphery of the member comprises applying ions onto the periphery with a charging device.

20. The method as in claim 18:

wherein the step of applying a charge to a first position on a periphery of the member comprises placing a second member into contact with the member to generate a triboelectric charge.

* * * * *